United States Patent [19]

Sakurai et al.

[11] Patent Number: 5,069,677
[45] Date of Patent: Dec. 3, 1991

[54] ABSORBENT ARTICLE

[75] Inventors: Akira Sakurai, Utsunomiya; Yasuhiro Torimae, Wakayama, both of Japan

[73] Assignee: Kao Corporation, Tokyo, Japan

[21] Appl. No.: 492,328

[22] Filed: Mar. 12, 1990

Related U.S. Application Data

[63] Continuation of Ser. No. 201,364, May 25, 1988, abandoned, which is a continuation of Ser. No. 829,155, Feb. 14, 1986, abandoned.

[30] Foreign Application Priority Data

| Feb. 15, 1985 | [JP] | Japan | 60-27891 |
| Feb. 15, 1985 | [JP] | Japan | 60-27892 |
| Feb. 15, 1985 | [JP] | Japan | 60-27893 |
| Jun. 21, 1985 | [JP] | Japan | 60-135660 |

[51] Int. Cl.$^5$ ............... A61F 13/15; A61F 13/20
[52] U.S. Cl. ............... 604/370; 604/365; 604/366; 604/367
[58] Field of Search ............... 604/358, 365, 366, 367, 604/370, 378, 381, 382

[56] References Cited

U.S. PATENT DOCUMENTS

| 3,056,406 | 10/1962 | Ness | 604/381 |
| 3,771,525 | 11/1973 | Chapuis | 604/381 |
| 3,881,489 | 5/1975 | Hartwell | 604/382 |
| 3,882,871 | 5/1975 | Taniguchi | 604/381 |
| 3,945,386 | 3/1976 | Anczurowski et al. | 604/370 |
| 3,967,623 | 7/1976 | Butterworth et al. | 604/370 |
| 3,976,074 | 8/1976 | Fitzgerald et al. | 604/370 |
| 4,015,604 | 4/1977 | Csillag | 604/382 |
| 4,287,251 | 9/1981 | King et al. | 604/370 |
| 4,417,893 | 11/1983 | Mizutani et al. | 604/370 |
| 4,480,000 | 10/1984 | Watanabe et al. | 604/370 X |
| 4,623,340 | 11/1986 | Luceri | 604/370 X |

Primary Examiner—Alan Cannon
Assistant Examiner—Elizabeth M. Burke
Attorney, Agent, or Firm—Birch, Stewart, Kolasch & Birch

[57] ABSTRACT

A sanitary article which comprises an absorbent layer, a leak-proof sheet and a surface sheet, at least one of the absorbent layer, leak-proof sheet and surface sheet having a porous aggregate of fibers integrated therewith.

5 Claims, 5 Drawing Sheets

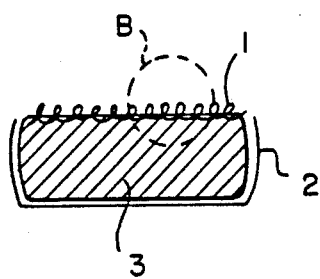
FIG. 1
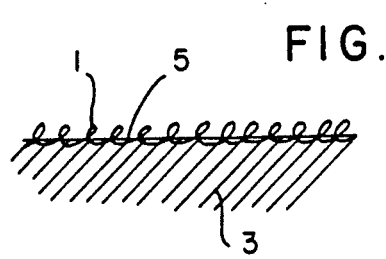
FIG. 2
FIG. 3
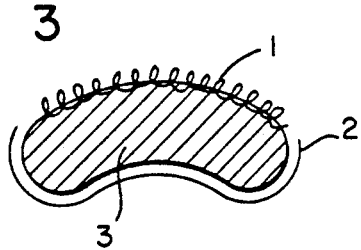
FIG. 4
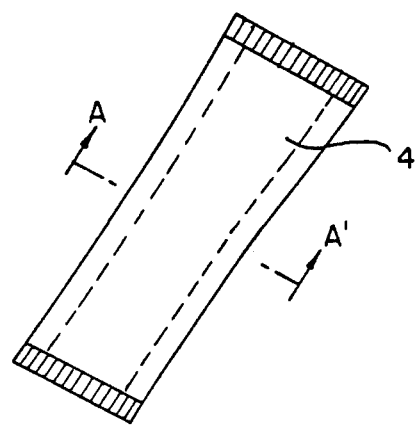
FIG. 5
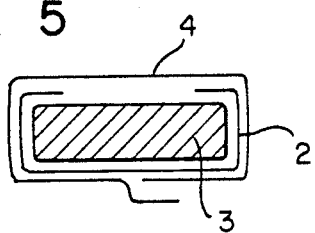
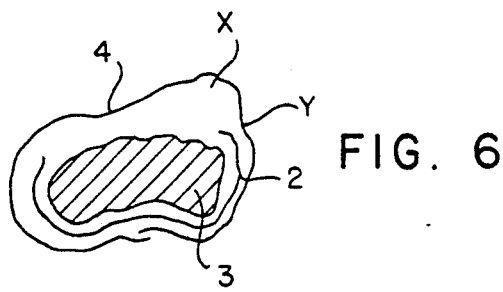
FIG. 6
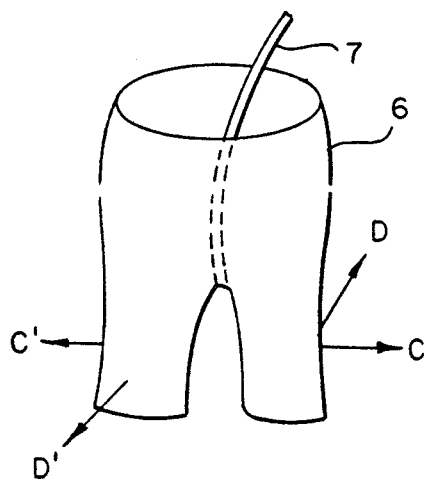
FIG. 7
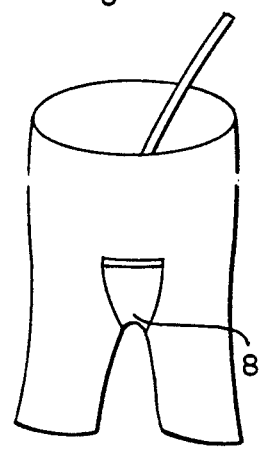
FIG. 8

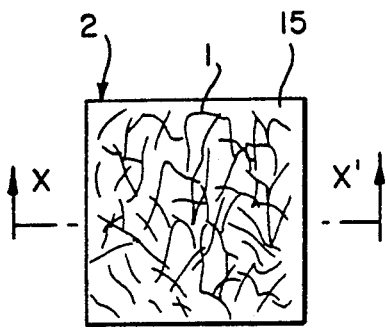
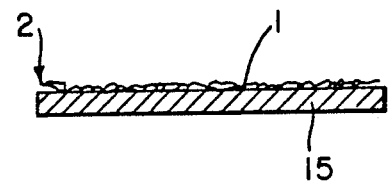
FIG. 9    FIG. 10
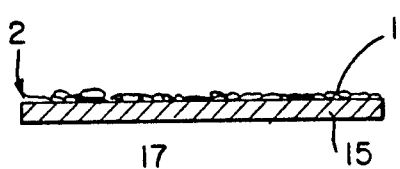
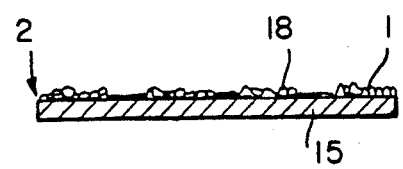
FIG. 11(a)    FIG. 11(b)
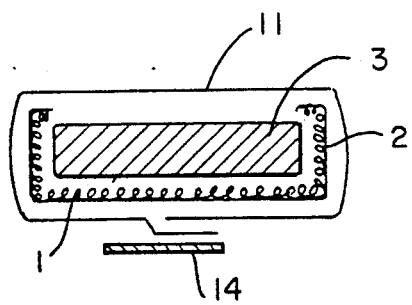
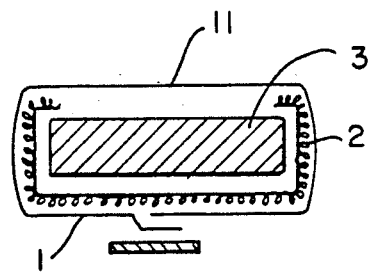
FIG. 12    FIG. 13
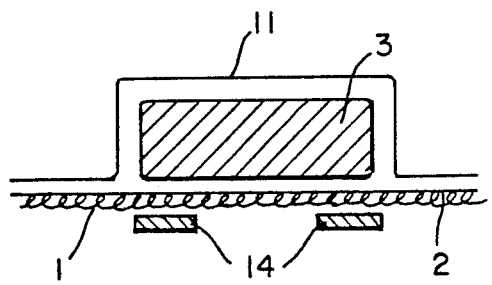
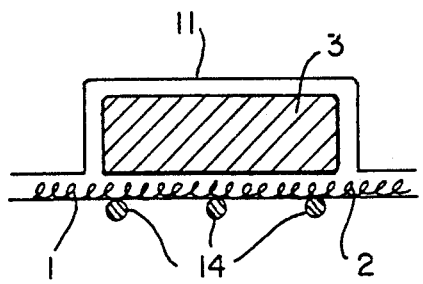
FIG. 14    FIG. 15

ABSORBENT ARTICLE

This application is a continuation of application Ser. No. 07/201,364 filed on May 25, 1988, which is a continuation of application Ser. No. 06/829,155 filed Feb. 14, 1986, both now abandoned.

The invention relates to an absorbent article such as a sanitary napkin, a disposable diaper and a paper diaper. The invention article is improved in feeling of touch on use, absorptivity, leakproof property, vapor permeability and water repellency.

BRIEF DESCRIPTION OF THE DRAWINGS

FIG. 1 is a lateral crosssectional view of an example of an absorbent article of this invention before use.

FIG. 2 is an enlarged view of portion B in FIG. 1.

FIG. 3 is a lateral crosssectional view of an absorbent article during its use.

FIG. 4 is a perspective view of an example of a conventional sanitary napkin.

FIG. 5 is a crosssectional view of a conventional sanitary napkin cut along a line A-A'.

FIG. 6 is a lateral crosssectional view of a conventional sanitary napkin during its use.

FIG. 7 is a perspective view of a movable female waist model.

FIG. 8 is a view showing a test specimen attached to the model. 1 is a fibrous aggregate. 2 is a leak-proof material. 3 is an absorbent layer. 4 is a sheet-like surface material. 5 is a portion where the fibrous aggregate is bonded (anchored) to the absorbent layer. 6 is a movable female waist model. 7 is an artificial blood dropping tube. 8 is a test specimen.

FIG. 9 is a planar view of one example of the leak-proof material according to the present invention.

FIG. 10 is a crosssectional view of it cut along a line X-X'.

FIG. 11 is a crosssectional view of another example of the leak-proof material according to the present invention.

FIGS. 12 and 13 are rough cross-sectional views of examples of the absorbent article of the present invention used as sanitary napkins.

FIGS. 14 and 15 are rough crosssectional views of examples of the absorbent article of the present invention used as disposable diapers. 11 represents a liquid-permeable surface material. 14 represents a pressure-sensitive adhesive (slip-prevention or fixation tape). 15 is a porous base material. 17 is an adhesive. 18 is a hot-melted portion.

FIGS. 28 and 29 show embodiments of the invention in which the fiber aggregates are integrated with the lowermost material.

FIG. 29 shows an embodiment in which the surface sheet does not completely cover the leakproof sheet.

FIG. 30 shows an embodiment in which the fibrous aggregate is elastic, a) is the worn napkin in side view; b) is the worn napkin in plane view.

STATEMENT OF PRIOR ARTS

Figure 16:
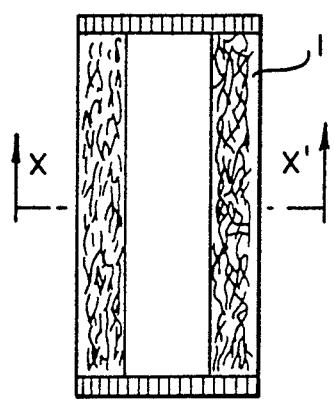
FIG. 16 is a planar view of an example of the absorbent article of the present invention.

The basic structure of a conventional absorbent article such as a sanitary napkin or a paper diaper consists of an absorbent layer 3 of cotton-like pulp, absorbent paper, a water-absorptive polymer, or the like; a leak-proof material 2 of a laminate sheet formed from a polyethylene film and a waterproof paper, a non-laminated polyethylene film, or the like; a sheet-like surface material 4 covering the surface thereof; and a slip preventing tape (fixation tape) for ensuring fixation thereof during its use.

Various performance characteristics required particularly of such an absorbent article can be mentioned. Among them, the most important are good absorptivity, which is essential, and little leakage. These are, of course, greatly affected by the properties of the surface material constituting the surface of the absorbent article. Accordingly, studies have been made with a view to improving the absorptivity of the surface material, namely raising the absorption rate to inhibit leaking out of the absorbent article owing to flow over of the surface thereof. Various achievements of these studies have been reported.

One example is the development of a heatbond type adhesive using a hot-melt fiber as a substitute adhesive material for a commonly used chemical binder, specifically an acrylic binder, the use of which causes reduction in the absorption rate. This type is now widely utilized.

As for the fiber to be used, in addition to rayon which has heretofore been commonly used, utilization of hydrophobic fibers such as polypolyethylene, conjugated polyethylene/polypropylene, polyester, polyamide, and polyacrylonitrile fibers is under investigations.

A relatively recent trend includes the development of methods of preparing a non-woven fabric according to a so-called spun-bonding system in which a sheet-like matter is formed by bonding of filaments, and utilizing a melt-blowing system as an application in which formation of an extremely fine fiber is possible these fabric are utilized in the field of absorbent materials.

Utilization of highly absorptive polymers such as acrylic type and starch type grafted polymers has been positively made for the purpose of improving the absorption capacity of the absorbent layer to prevent leakage due to an insufficient absorption capacity. As a result, the absorption capacity of the absorbent layer itself is improved, and it is believed that occurrence of leakage due to the insufficient absorption capacity is largely suppressed. However, this indicates that the countermeasure against leakage on the side of the surface material, including how to guide menstrual blood or urine to the absorbent layer, becomes important all the more.

In view of the above, consideration will be given to the surface material once again while bearing its configuration in mind. In conventional structures, the surface material is one preliminarily formed into a sheet, which is subjected to lamination, insertion, and fixation to obtain an absorbent material according to the prior art technique.

As a result of observing of the actual absorption states of absorbent articles, it was found that leakage occurred even in, for example, a sanitary napkin comprising a surface material having a high absorption rate as measured with only the surface material itself, and an absorbent layer having a sufficient absorption capacity.

The present inventor's detailed analysis of the cause of this revealed that the absorbent layer which is set in crotch form (namely with kinks in the absorbent layer) appears because absorbent layer is in a deformed state following the movement of the crotch, during for example walking. On the other hand, the surface material does not take a concerted behavior as the covering sheet. Therefore, a space X is formed between the surface material 4 and the absorbent layer 3 as shown in FIG. 6, though the surface material and the absorbent layer should intrinsically take a configuration of being mutually laminated in contiguity. As a result, menstrual blood excreted onto the surface material 4 cannot be effectively guided to the absorbent layer 3 and remains on the surface material 4. Since the surface material 4 has a basis weight of about 20 g/m² and hence a small absorption capacity in itself, it cannot absorb nor retain the blood. Therefore, the blood flows (diffuses) in various directions over the surface material 4 as shown in FIG. 6Y, resulting in the occurrence of leakage. Accordingly, it is important in the leak-preventing measure to always keep the absorbent layer 3 and the surface material 4 in an integrated state even against the movement of the crotch in complex form.

In the case of a thick surface material (e.g., a type of weakly bonding reverse face) effective as one means for preventing stickiness (reversal of a liquid once absorbed onto the surface) during its use prevention of which is required in an absorbent material as well, fixation of the absorbent layer and the surface material is additionally necessary. A plausable means therefor is fixation by heat-rolling the effective surface of a surface material on an absorbent layer or by using an adhesive. However, since it is impossible to completely prevent formation of solid matters from a heat melt or the adhesive, a poor feeling in its use ensues. Besides, since a fixation area cannot be sufficiently secured because of the role of an absorbing surface, the above mentioned concerted behavior against movement in a complex form is not exhibited. Thus the abovementioned means can not present any essential solutions to the problems encountered in the prior art.

When the amount of menstrual blood is small, choice of a surface material has only to be made with consideration given to the hand rather than the absorptivity. Specifically, a small fiber diameter and a low real weight are favorable. However, a non-woven fabric having such properties is weak in respect to strength, and shows large elongation even under a low load, leading to notably poor processability with a napkin-forming machine. Thus, such a non-woven fabric cannot be employed and is not being employed in fact.

As described above, according to the conventional technique, no effective leak-proof measure cannot be found when consideration is given to movement during its use. As to paper diapers, the same phenomenon has also been found.

As disclosed in Japanese Patent Publication No. 39,134/1984 and Japanese Patent Laid Open No. 147,695/1979, there are techniques of inhibiting diffusion of excretions through the absorbent layer, the liquid-permeable surface material, or both. However, these techniques are ineffective in side leak occurring due to diffusion of the excretions inside the surface material.

A technique of covering part of the surface material with a water-impermeable sheet is disclosed in Japanese Utility Model Laid-Open No. 75,317/1980, etc. In this case, however, when an absorbent article is in service, water generated by sweating from the skin or the like remains in the water-impermeable sheet and hence not only gives a user a feeling of stuffiness or discomfort but also provides a fear of causing her or him to get a disease such as a rash or an inflammation, thus presenting new problems.

This invention mainly aims at preventing an absorbent article from causing side leakage or oozing. Side leakage in the absorbent article will be further illustrated by way of a sanitary napkin as an example.

Figure 26A:
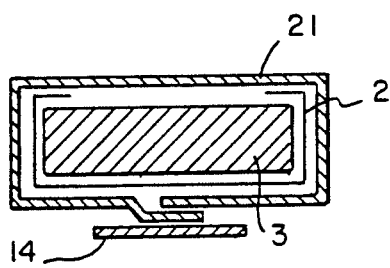
FIG. 26 shows an example of a conventional sanitary napkin, and includes (a) a lateral crosssectional view showing the state thereof before use and (b) a lateral crosssectional model diagram showing occurrence of side leak on the assumption of the state of use.
Figure 26B:
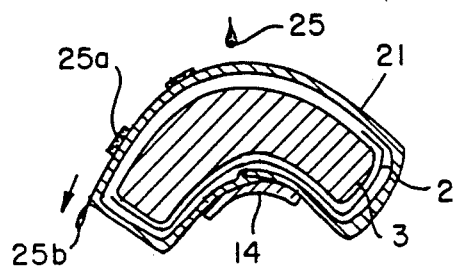
Figure 27A:
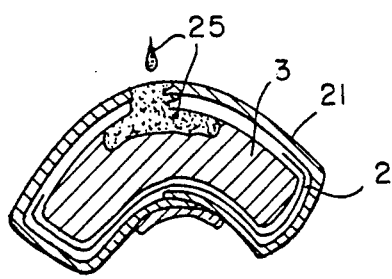
FIG. 27 shows an example of a conventional sanitary napkin having an improved surface material, and includes (a) a lateral crosssectional model diagram demonstrating the same absorption feature thereof as in FIG. 26 (b) and (b) a lateral crosssectional model diagram demonstrating occurrence of side leak caused by flow of blood turned back from the absorbent layer over the surface of the non-woven fabric.
Figure 27B:
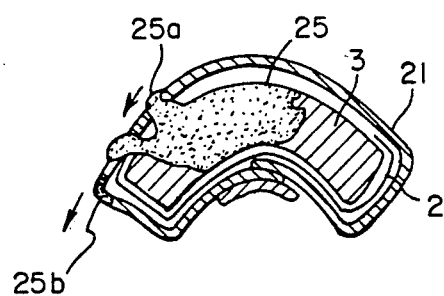

In general, as shown in FIG. 26(a) a sanitary napkin has a structure comprising a leak-proof material 2 covering the lower and side faces of and part of the upper faces of an absorbent layer 3, a liquid-permeable surface material 21 wrapping both of them, and a slip-preventing tape 14 attached to the lowermost face. In service, the sanitary napkin is put into a V form in the center, as shown in FIG. 26(b). In a binder type napkin in which a conventional acrylic pressure-sensitive adhesive is used as the surface material 21, therefore, the side leakage frequently occurs with flow of menstrual blood 25 on the upper surface of the surface material 21 in the direction of 25a to 25b, as shown in FIG. 26(b), since it is low in absorption rate. However, a surface material having a high absorption rate and a low surface wettability, for example, with the use of a polyolefin fiber has recently been developed. This has resulted in the menstrual blood 25 which hardly flows to the surface of the surface material 21 as shown in FIG. 26(b), and is well absorbed in the absorbent layer in such a way as shown in FIG. 27(a). Where the menstrual blood capacity of the absorbent layer 3 is small, or where the menstrual blood diffusion rate is slow, however, menstrual blood 25 present around just under the surface material 21 is pushed out over the surface as shown in FIG. 27(b). Thus the surface material 21 must absorb the menstrual blood pushed out again. The menstrual blood 25a absorbed in the surface material again diffuses in spaces between fibers constituting the surface material 21 in various directions, causing the side to leak or ooze.

Figure 28A:
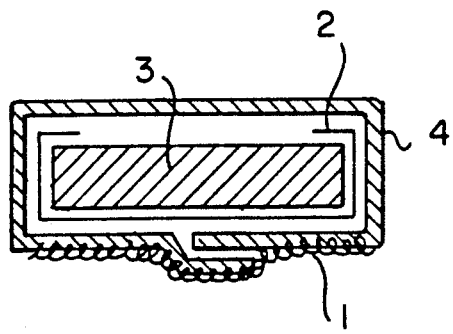
FIG. 28a shows an embodiment with fiber aggregates integrated on the lower surface of the napkin.
Figure 28B:
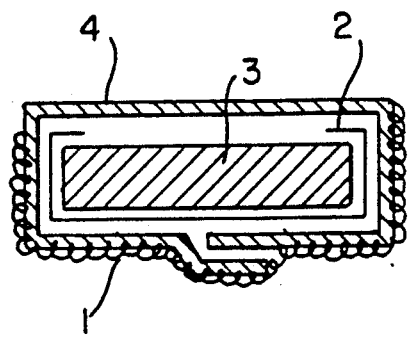
FIG. 28b shows fiber aggregates over the entire surface except for where the napkin contacts the user.
Figure 28C:
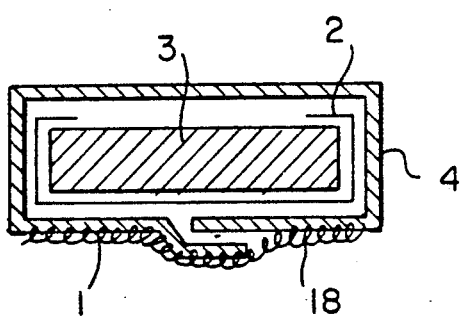
FIG. 28c shows fiber aggregates integrated by melting.
Figure 28D:
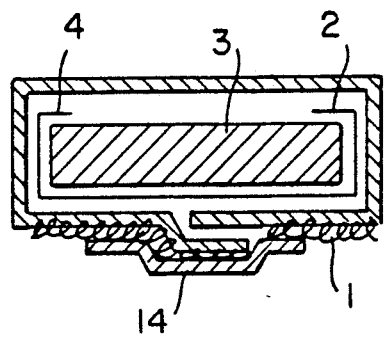
FIG. 28d shows an embodiment of the napkin with adhesive for attachment.

Further, the worn napkin does not keep a flat form, so that many wrinkles are formed in both the end portions along the long sides, naturally leading to formation of grooves 26, as shown in FIGS. 28(a) and (b). Once the grooves 26 are formed, the napkin does not restore to the original flat form. The grooves 26 are rather liable to grow distinct since the napkin is folded in the positions of the grooves 26 in following a change of the form of a crotch. Therefore, menstrual blood in apt to leak along the grooves 26, providing another cause of side leakage.

These causes are common between the sanitary napkin and a disposable diaper, though menstrual blood is different from urine and loose feces in its entity and the form of the crotch and hence the wearing pressures are different between women and infants as, the wearers.

Conventional absorbent articles such as sanitary napkins and disposable diapers have a leak-proof material provided under an absorbent layer for the purpose of preventing excreta such as menstrual blood or urine from leaking or oozing out of the absorbent article.

Common leak-proof materials which have been employed include laminate papers composed of a waterproof paper such as a wet-sized paper, a wet-spunbonded non-woven rayon fabric, or dry-binder-bonded non-woven fabric, and a film of a thermoplastic resin such as polyethylene, modified polyethylene, or an ethylene-vinyl acetate copolymer, laminated on said waterproof paper; and, in some cases, one of the above-mentioned films used by itself. Use of a leak-proof material made of a porous film prepared by stretching a blend of a polyolefin resin with a filler and a liquid rubber has recently been proposed.

When an absorbent article is worn for use, the amount of excreta, such as menstrual blood or urine, absorbed by the absorbent article hardly decreases but possibly increases until it is exchanged. Particularly when the above-mentioned laminate paper or film itself is used as the leak-proof material, the excretions can not escape by evaporation from the lower face of the absorbent article since the leakproof material is positioned under the absorbent layer. Even though the excretion can evaporate a little through the effective face of the absorbent article, the effect of evaporation can hardly be expected in reality. Therefore, even if the excretions absorbed in the absorbent article evaporate with the aid of the body temperature, almost all of it remains inside the system. Thus the user frequently feels stuffy and unpleasant. Besides, diseases such as rashes or inflammations are sometimes caused by stuffiness during the use of such an article. In general, the requisites of a comfortable leak-proof material includes a vapor permeability of 0.5 g/100 cm$^2$.hr or more in the case of a napkin, or 1 g/100 cm$^2$.hr or more in the case of a diaper, and a leak-proof capacity of 70 g/cm$^2$ or more in the case of a napkin, or 100 g/cm$^2$ or more in the case of a diaper (the measurement methods therefor will be described later). The cause of the feeling of unpleasantness in the case of the above-mentioned leak-proof material is particularly related to the vapor permeability.

Where the porous film, prepared by stretching a blend of a polyolefin resin with a filler and a liquid rubber, is employed as the leak-proof material, the unpleasant feeling of the user can be diminished and diseases such as rash or inflammation are hardly caused. However, there have been pointed out such difficult problems in the manufacture of the film that a high level of control precision in the manufacture is required, and that the cost is high.

Where the film by itself or the porous film is employed as the leak-proof material, insertion of it is not easy in the manufacture of absorbent articles because the film itself has no nerve, and longitudinal wrinkles are liable to be formed and remain as such in a product when tension is applied on it. Besides, a feeling of discomfort in its use is pointed out because it provides a rustling noise during use.

SUMMARY OF THE INVENTION

In a sanitary article of the invention which comprises an absorbent layer, a leak-proof sheet and a surface sheet, the surface sheet or the leakproof sheet comprises a porous fiber aggregate. The fiber aggregate has been integrated by melting the fibers and fixing them onto the absorbent layer, the surface sheet or the leak-proof sheet.

A sanitary article according to the invention also comprises an absorbent layer, a leak-proof sheet and a surface sheet, at least one of both sheets having a porous aggregate of hydrophobic fibers integrated thereon or on the absorbent layer by melting and fixing of said fibers.

According to the invention, the invention provides the following, preferable, practical embodiments. (1) The fiber aggregate has been integrated on the surface with the absorbent layer. The fiber aggregate may serve as the surface sheet. Alternatively another surface sheet may be used in addition to the absorbent layer on which the fiber aggregate has been integrated. (2) The fiber aggregate has been integrated with a porous material to form the leak proof sheet below the absorbent layer. (3) The fiber aggregate has been integrated with a liquid-permeable surface sheet to form the surface sheet. (4) The fiber aggregate has been integrated with the lowermost material such as a surface sheet on the back side.

The invention will be illustrated in reference to the above shown embodiments and the hereto attached drawings.

EMBODIMENT 1

As a result of intensive investigations with a view to obviating the defects of the conventional absorbent articles, namely to developing an absorbent article having excellent absorptivity, especially excellent leak-proof characteristic, and excellent feeling in its use, the present inventors have completed the present invention.

Specifically, the present invention concerns an absorbent article characterized in that an absorbent layer is integrated with a fibrous aggregate which constitutes the surface of said absorbent article and has interfiber spaces, wherein the integration is effected by fiber welding in a portion where said fibrous aggregate is in contact with said absorbent layer.

The absorbent article of the present invention will now be described in detail with reference to the attached drawings. FIG. 1 is a lateral crosssectional view of an example of the absorbent article of this invention. FIG. 2 is an enlarged view of it in the B portion.

In the present invention, a fibrous aggregate 1 is integrated with an absorbent layer 3 by fiber welding in a position 5 where both are in contact with each other. Since fixation is not effected with heat melting or a chemical binder such as an adhesive as has heretofore been used, the absorptivity and the feeling of use are not spoiled. Various methods of integration of the fibrous aggregate with the surface of the absorbent layer are possible, and include one comprising ejecting a hot-melt resin in a molten state through minute openings and one comprising preparing a solvent solution of a resin soluble in the solvent and ejecting the same through a nozzle of a high-pressure spray. Any one of these methods can be utilized in so far as integration of the fibrous aggregate can be effected. In the melting method, a resin is melted above the melting point thereof, and the resultant molten resin is ejected together with air at a temperature of 200° to 400° C. through a nozzle having a plurality of fine openings of 100 to 500 μm, usually 200 μm, onto the absorbent layer. The ejected system is stretched to become fine matters. In the solvent method, a resin is dissolved in a solvent, and sprayed according to an airless or air spray procedure as usually used, followed by drying. Any solvent may be used herein in so far as it can dissolve the resin. However, tetrahydrofuran, toluene, and demethylformamide are desirable from the viewpoint of workability.

Polymer substances capable of being ejected through fine openings by any one of various means can be basically used as the fiber material from which the fibrous aggregate involved in the present invention is to be formed. They include polyethylene, polypropylene, ethylene-vinyl acetate copolymers (EVA), polyesters, polyurethanes, polybutadiene, and modified products thereof. Choice of the material can be made depending on the purpose of application and the designed performance. The material is not limited to a single component.

As to formation of the fibrous aggregate, the aggregate is not limited to a single layer, and may consist of a plurality of layers depending on the desired performance, the hand, etc.

The fiber diameter, density, and weight of the aggregate to be formed are not particularly limited. However, the fiber diameter is preferably 1 to 40 μm, more preferably 3 to 20 μm. A smaller fiber diameter in the outermost surface (in the case of a single layer, the layer itself) is especially effective in improving the hand. A lower fiber density (large interfiber spaces of the formed aggregate) is favorable for improving the absorptivity for a highly viscous matter.

Utilization of a surface-active agent, a coloring material, and embossing according to need is not excluded if desired.

The raw material and configuration of the absorbent layer, leak-proof material, etc. of the absorbent article are not limited as well.

In the absorbent article formed by integrating the fibrous aggregate as the surface material with the surface of the absorbent layer in the abovementioned manner, separation of the surface material and the absorbent layer during its use, does not occur, unlike the conventional absorbent article as described above. Since the fibrous aggregate 1 is always disposed on the surface of the absorbent layer without detriment to the function of the aggregate in effectively guiding menstrual blood to the absorbent layer as shown in FIG. 3, leakage during its use, particularly during active movement, can be notably prevented.

EMBODIMENT 2

The present invention has been made with a view to providing an absorbent article which obviates the defects of conventional ones and is beneficial to consumers. Specifically, it concerns an absorbent article in which a leak-proof material, not requiring so high a level of manufacturing technique and having excretion impermeability and a vapor permeability, is employed.

More specifically, the absorbent article of this invention comprises an absorbent layer and a leak-proof material provided under said absorbent layer, wherein the leak-proof material is prepared from a porous base material and a fibrous aggregate of a hydrophobic fiber with interfiber spaces integrated together by fiber welding in a portion where the fibrous aggregate is in content with the porous base material.

Embodiments of the absorbent article of this invention will now be described with reference to the drawings.

FIG. 9 is a plan view of an example of a leak-proof material to be used in the absorbent article of this invention. FIG. 10 is a cross-sectional view of a leak-proof material cut along a line X-X'. The leak-proof material 2 is formed by integration of a porous base material 15 and a fibrous aggregate 1 of a hydrophobic fiber. As enlarged in FIG. 9 for the purpose of facilitation of understanding, the fibrous aggregate 1 has spaces provided between adjacent fibers. Therefore, excretion is prohibited from passage due to the hydrophobic nature of the fiber and the leak-proof effect of the porous base material, whereas vapor can pass through interfiber spaces and pores of the porous base material.

The porous base material to be used in the present invention is desired to have a certain strength by itself. Specific examples of it include paper, porous films, knitted fabrics, woven fabrics, and non-woven fabrics. The porous base material need not necessarily be made of a single material, but may contain a filler such as calcium carbonate. A water-repelling treatment of at least the surface of the porous base material with a sizing agent or the like provides an increased effect. Specifically, the leak-proof effect is desired to be 30 $g/cm^2$ or more, while the vapor permeability is desired to be 1 $g/100\ cm^2.hr$ or more.

A hydrophobic fiber is desirable as the fiber constituting the fibrous aggregate. The fiber is desired to have thermoplasticity and solvent solubility so that it can be suited for the integration as described later. Specific examples of the fiber include those of polyethylene, polypropylene, polyesters, nylons, ethylene-propylene rubbers, polyurethanes, polybutadiene, high styrene, vinylidene, polyvinyl chloride, and acetate. The size of the fiber, which is influential on the size of spaces formed between adjacent fibers, is desired to be 1 to 40 μm, preferably 3 to 20 μm. The weight of the fibrous aggregate is 3 to 50 $g/m^2$, preferably 5 to 30 $g/m^2$ since it does not need so-called nerve in itself and since too large a size of it may affect the vapor permeability.

The melting method and the solvent method are preferred as the method of integrating the porous base material with the fibrous aggregate. In the melting method, a hot-melt resin is molten by heating the same up to a temperature higher than the melting point thereof, and then ejected onto the porous base material through a small opening nozzle to solidify is a fibrous form on the porous base material for integration thereof with the porous base material. In the solvent method, a resin is dissolved in a solvent, and sprayed over the porous base material with the aid of air as usual or without it, followed by drying to remove the solvent. According to either of these methods, the porous base material and the fibrous aggregate are integrated substantially all over the surface. Any solvent may be used in so far as it can dissolve therein the fiber constituting the fibrous aggregate. However, from the viewpoints of availability and ease in handling, tetrahydrofuran (THF), dimethylformamide (DMF), toluene, acetone, hexane, ethyl acetate, etc. are recommendable.

The methods of integration of the porous base material with the fibrous aggregate may possibly include one using an adhesive and one utilizing heat embossing. However, since these methods can not provide interfiber spaces, they are not quited to production of the leak-proof material to be used in this invention. However, combined use of one of these methods with the melting method or the solvent method is not excluded. More specifically, part of integration may be done by bonding with an adhesive 17 as shown in FIG. 11(a), or heat-welded portions 18 may be locally provided by heat embossing as shown in FIG. 11(b). In this case, however, the portions where the adhesive or the heat embossing is applied are desired to account for 40% or less when consideration is given to interfiber spaces and hand.

Various embodiments of the absorbent article of the invention are shown in FIGS. 12 to 15. FIG. 12 shows an example of the absorbent article of this invention used as a sanitary napkin. In this example, a leak-proof material 2 is provided under an absorbent layer 3, and the both are covered with a liquid-permeable surface material 11 such as a non-woven fabric. A pressure-sensitive adhesive 14 is provided in a lowermost layer for convenience of wearing. In this case, the leak-proof material 2 covers the side face and part of the upper face of the absorbent as well. However, this is not always necessary. Covering of only the bottom face of the absorbent material will suffice. FIG. 13 shows substantially the same view as in FIG. 12. The fibrous aggregate 1 is, however, provided on the side of the absorbent layer 3 in FIG. 12, while it is provided on the side of the surface material 11 in FIG. 13. FIG. 14 shows another embodiment of the absorbent article of this invention. A leak-proof material 2 is provided under an absorbent layer 3, and a liquid-permeable surface material 11 does not cover the leak-proof material 2. This is mainly a case where the absorbent article is used as a disposable diaper. However, it can, of course, be used as a sanitary napkin having the same configuration. FIG. 15 shows substantially the same view as in FIG. 14. The fibrous aggreage 1 is, however, provided as a lowermost layer in FIG. 14, while the fibrous aggregate 1 is in contact with the absorbent layer 3 in FIG. 15.

Since a sheet of a porous base material and a fibrous aggregate with interfiber spaces integrated together is employed as the leak-proof material in the absorbent article according to the present invention, vapor evaporating from human excretions passes through interlayer spaces and pores of the porous base material to escape out of the system, though the absorbed excretion themselves can not pass through the leak-proof material to ooze out of the system. Thus the absorbent article does not give a feeling stuffiness during use, and provides an excellent feeling during use. Particularly when an elastic resin such as nylon, ethylene-propylene rubber, polyurethane, or 1,2-polybutadiene is used in the fibrous aggregate, the friction coefficient of the fibrous aggregate is high, leading to markedly reduced slip between the absorbent layer and the leak-proof material or between the leak-proof materials. Thus an additional effect can be recognized in respect of both shape retention and leak prevention.

EMBODIMENT 3

The invention has been made with a view to solving the above-mentioned problems. Specifically, the absorbent article of the present invention comprises an absorbent layer and a liquid-permeable surface material provided on the upper side thereof, wherein said material is provided at least on the upper side of both the end portions of the absorbent layer and is integrated with a fibrous aggregate of a hydrophobic fiber with interfiber spaces by fiber welding in a portion where the fibrous aggregate is in contact with the surface material.

The absorbent article of this invention will now be described in detail with reference to the drawings.

Figure 17:
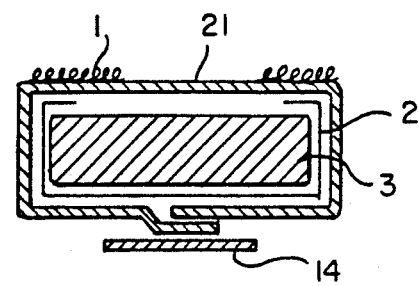
FIG. 17 is a crosssectional view of it cut along a line X-X'.

FIGS. 16 and 17 show an example of the absorbent article of this invention applied to a sanitary napkin. This structure can, of course, be applied to a disposable diaper. An absorbent layer 3 is covered, on the lower and two side faces and on the two upper face end portions, with a leak-proof material 2. The whole of them are covered with a surface material 21. A slip-preventing rape 14 is provided on the lowermost layer. A fibrous aggregate 1 of a hydrophobic fiber is provided on the liquid-permeable surface material 21 provided in the two end portions over the absorbent layer 3. The fibrous aggregate is integrated with the surface material 21 by welding. The fibrous aggregate 1 has many spaces present between fibers as is apparent from FIG. 16.

The liquid-permeable surface material that can be used in the present invention is not particularly specified. However, a non-woven fabric is preferred from the viewpoint of availability. The material of the non-woven fabric may be either a hydrophilic material such as rayon or a hydrophobic material such as polyolefin. The process of preparing the non-woven fabric is not limited, and may be any one of, for example, the wet process, the dry process, the spun-bonding process, and the punching process.

The fiber constituting the fibrous aggregate must be hydrophobic in nature, and it is desirable to have thermoplasticity and solvent solubility so that it.is suited to the method of integration as will be described infra. A wide variety of materials can be employed, and they include olefin, urethane, ester, amide, vinyl acetate, and acrylic types. Specific examples include polyethylene, polypropylene, polyesters, nylon, ethylene-vinyl acetate copolymers, polyurethanes, polybutadiene, high styrene, vinylidene, ethylene-propylene rubbers, and acetate, which are usable since they can be ejected through a nozzle to form a fibrous aggregate. Among others, polyethylene, polypropylene, polyesters, and ethylene-vinyl acetate copolymers are recommendable from the viewpoints of cost and processability, while elastic polyurethane, polybutadiene, and ethylene-propylene rubbers are recommendable from the viewpoint of little wrinkling. The fiber size is preferably small since it is influential on the size of spaces formed between adjacent fibers, which is desired to be small. Thus it is preferably 1 to 40 μm with further consideration for hand, more preferably 3 to 20 μm from the additional viewpoint of processability. Use of a water-repelling treatment agent, a clouding agent, a pigment, etc. in the fiber is not excluded.

As the amount of the fibrous aggregate to be integrated with the liquid-permeable surface material is increased, the side leak-preventing effect is enhanced.

Thus it is preferably 5 to 50 g/m². Although the width of the fibrous aggregate is not limited in principle, it is desirably 5 mm or more for a better effect. A width of the fibrous aggregate per end portion is desirably ⅓ of that of the sanitary napkin from the viewpoint of clear allotment of menstrual blood receiving portions.

The melting method and the solvent method are preferred as the method of integrating the liquid-permeable surface material with the fibrous aggregate. In the melting method, a hot-melt resin is melted by heating the same up to a temperature higher than the melting point thereof, and then ejecting onto the liquid-permeable surface material through a small opening nozzle to solidify in a fibrous form on the liquid-permeable surface material for integration thereof with the liquid-permeable surface material. In the solvent method, a resin is dissolved in a solvent, and sprayed over the liquid-permeable surface material with the aid of air as usual or without it, followed by drying to remove the solvent. According to either of these method, the liquid-permeable surface material and the fibrous aggregate are integrated with each other. Any solvent may be used in so far as it can dissolve therein the fiber constituting the fibrous aggregate. However, from the viewpoints of availability and ease in handling, tetrahydrofuran (THF), dimethylformamide (DMF), toluene, acetone, hexane, ethyl acetate, etc. are recommendable.

Figure 19:
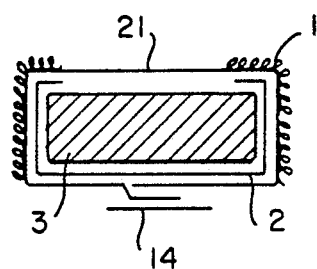
FIGS. 19 to 25 are rough crosssectional views of other examples of the absorbent article of the present invention.

The methods of integration of the liquid-permeable surface material with the fibrous aggregate may possibly include one using an adhesive and one utilizing heat-embossing. However, since these methods can not provide interfiber spaces, they are not suited in this invention. However, combined use of one of these methods with the melting method or the solvent method is not excluded. In this case, however, the portions where the adhesive or the heat-embossing is applied are desired to account for 40% or less when consideration is given to interfiber spaces and hand. FIG. 19 shows another embodiment. The embodiment is substantially the same as in FIG. 17, but different from that of FIG. 17 in that the fibrous aggregate 1 is provided on the side faces of the sanitary napkin as well. The embodiment of FIG. 19 is more effective in the side leakage prevention.

Figure 20:
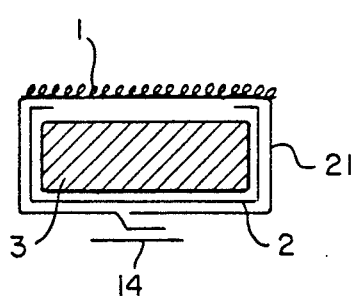
Figure 21:
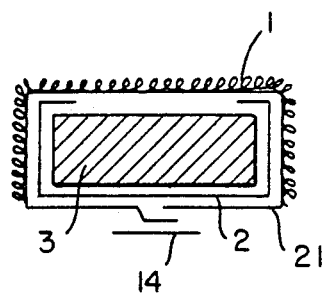

FIGS. 20 and 21 show further embodiments, and correspond to FIGS. 17 and 19, respectively. The fibrous aggregate 1 is provided on a middle portion of the upper face of the liquid-permeable surface material 21 as well. The fibrous aggregate provided on that middle portion is satisfactory only if it provides a hydrophobic nature to the liquid-permeable surface material 21. When it is too thick, it unfavorably hinders for liquid permeation. Thus its amount is preferably 3 to 5 g/m².

Figure 22:
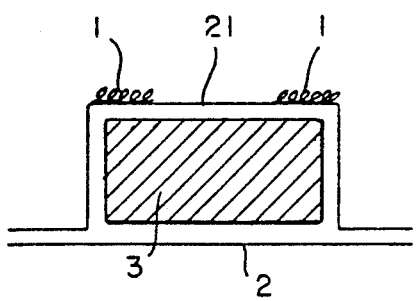

FIG. 22 shows an example of the absorbent article of this invention mainly applied to a disposable diaper. This structure can, of course, be applied to a sanitary napkin. In this structure, a leak-proof material 2 wider than the lower face of an absorbent layer 3 is provided on the lower face of the absorbent layer 3, and a liquid-permeable surface material 21 is provided in such a way as to cover the absorbent layer 3 and the leak-proof material 2. If necessary, a fixation tape or a slip-preventing tape may be attached.

Figure 23:
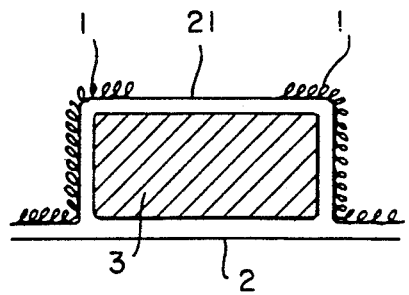
Figure 24:
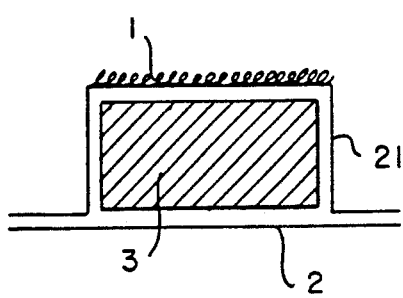
Figure 25:
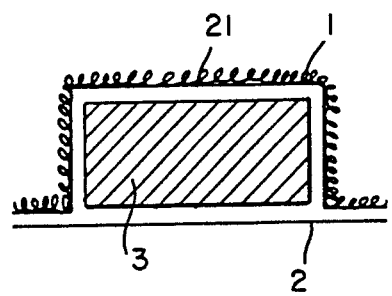

FIGS. 23, 24 and 25 show embodiments corresponding to FIGS. 19, 20 and 21, respectively. In FIGS. 25 and 23, the fibrous aggregate 1 is provided on the liquid-permeable surface material 21 above the leak-proof material 2 as well. The fibrous aggregate present in this position can be dispensed therewith.

Figure 18:
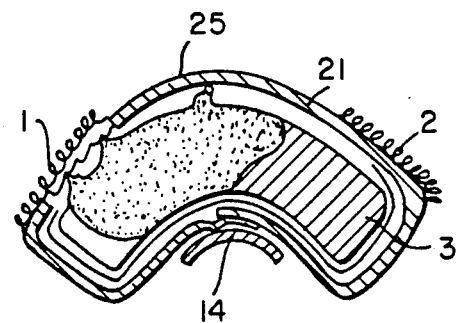
FIG. 18 is a lateral crosssectional view showing the mechanism of side leak prevention.
Figure 30A:
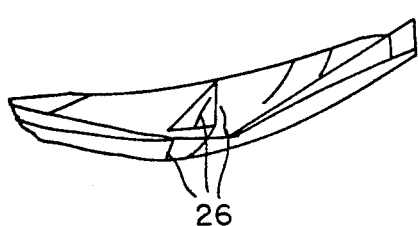
FIG. 30 shows the state of a worn napkin 1 and includes (a) a side view thereof and (b) a plan view thereof. 21 represents a surface material. 25 represents blood. 25a represents blood diffusing on the surface material or partially in the surface material. 25b represents side-leaked blood. 26 are grooves formed in the end portions on the sides (long sides) of napkin.
Figure 30B:
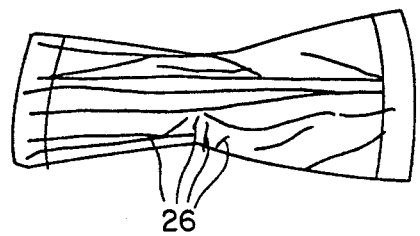

The absorbent article of this invention has a structure as hereinbefore described. Therefore, even when excretion, such as menstrual blood or urine, once absorbed in the absorbent layer, are absorbed by the surface material 21 again as shown in FIG. 18, the excretion do not leak therefrom since diffusion of the excretions through the surface material is slight due to the fibrous aggregate 1 welded with the surface material 21, and since the fibrous aggregate 1 is hydrophobic. This way side leak prevention is greatly achieved. Furthermore, since the fibrous aggregate has interfiber spaces, it has leak-proof properties against excretions, and, nevertheless, is not spoiled in air permeability. Thus the absorbent article can be comfortably used since it does not provide stuffiness in its use.

Where the fibrous aggregate is elastic, wrinkles are hardly formed in the long side portions during the service as shown in FIGS. 30(a) and 30(b). Also in this respect, the absorbent article is excellent in side leak prevention.

EMBODIMENT 4

The invention further includes an embodiment in which the fiber aggregates have been integrated with the lowermost sheet, that is, on the side not to come into contact with the skin of a user. This article is effective to prevent itself from slipping and easy to apply to a portion as a user desires. It does not slip out of an underwear of a user because of the uneven back surface. It therefore offers feeling of closeness and softness to a user. The article solves problems in the state of arts in respect to an adhesive tape. As a result, the article of the embodiment 4 prevents the absorbed liquid from leaking out.

Figure 29:
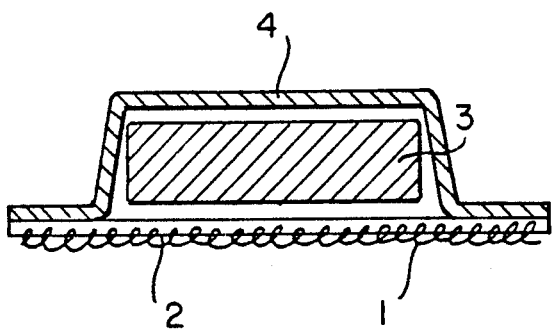

FIGS. 28 and 29 show the article. FIG. 28a shows an article having the fiber aggregates 1 integrated on the lowermost surface thereof, that is, on the surface sheet 4 on the back side. FIG. 28b shows an article in which the fiber aggregates have been provided over all of the surface except for a portion to come to contact with the skin of a user, including both side surfaces. FIG. 28c shows another embodiment in which the fiber aggregates 1 have been strongly integrated by melting of the fibers at portions 18. FIG. 28d shows an embodiment further comprising an adhesive tape 14 to serve a user. FIG. 29 illustrates an embodiment in which a surface sheet 4 does not extent to a leak-proof sheet 2 and the fiber aggregates 1 have covered the leak-proof sheet. This is suitable for a disposable diaper and useful also for a sanitary napkin and other applications.

The invention article will be illustrated in reference to examples thereof and the drawings.

Fibrous aggregates to be used in Examples according to the present invention and non-laminated sheets obtained from non-woven fabrics under the same conditions without integration thereof with the surface of the absorbent layer and to be used in Comparative Example are indicated in Table 1. Surface materials obtained according to customary processes and to be used in the Comparative Example are indicated in Table 2.

TABLE 1

| Sample code | Resin | Fiber formation system | Average fiber diameter (μm) | Basis weight (g/m²) | Non-laminated[*1] sheet |
| --- | --- | --- | --- | --- | --- |
| A | polyethylene | hot-melt type | 11 | 10 | |
| B | | | 16 | | |
| C | | | 22 | | |
| D | | | 11 | 20 | D' |
| E | | | 14 | | E' |
| F | | | 22 | | F' |
| G | | | 15 | 35 | G' |
| H | | | 23 | | H' |
| I | polyester | | 12 | 20 | I' |
| J | | | 19 | | J' |
| K | | | 23 | | |
| L | polyurethane | | 10 | 15 | |
| M | | | 15 | | |
| N | | solvent type with use of THF (tetrahydrofuran) | 11 | 18 | N' |
| O | | | 16 | | O' |
| P | | | 21 | | P' |
| Q | | | 16 | 35 | Q' |
| R | | | 22 | | R' |
| S | polypropylene | hot-melt type | 14 | 20 | S' |
| T | ethylene-vinyl acetate copolymer | | 17 | 20 | T' |
| U | polybutadiene | solvent type with THF | 9 | 20 | U' |
| V | | | 12 | | V' |
| W | | hot-melt type | 14 | 35 | W' |
| X | | | 20 | | X' |

(Note)
[*1]Non-laminated sheets formed on a release paper under the same conditions unlike formation of a fibrous aggregate on the surface of an absorbent layer are indicated by a prime attached to the corresponding sample codes.

TABLE 2

| Sample No. | Fiber (I) | Fiber (II) | Preparation system | Average fiber diameter (μ) | Basis weight (g/m²) |
| --- | --- | --- | --- | --- | --- |
| 1 | rayon | — | dry binder | 20 | 18 |
| 2 | rayon | rayon | | 17 | 35 |
| 3 | rayon | ES | dry heat bonding | 19 | 18 |
| 4 | | | | | 35 |
| 5 | polypropylene | ES | | 16 | 18 |
| 6 | | | | 22 | 18 |
| 7 | | | | 22 | 35 |
| 8 | ES | — | | 22 | 20 |
| 9 | rayon | — | wet spun bonding | 19 | 27 |
| 10 | polyester | — | spun bonding | 12 | 18 |
| 11 | | | | 12 | 30 |
| 12 | polyethylene | — | melt-blow | 13 | 18 |
| 13 | | | | 13 | 30 |

EXAMPLE 1

Use: Regular Type Sanitary Napkin

A laminate of an absorbent layer composed of cotton-like pulp (2.5 g), 4 sheets of absorbent paper (2 g), and water-absorptive polymer (0.3 g) and a leak-proof material consisting of water-proof paper having 8 μm polyethylene laminated was used as a base structure.

Articles according to the present invention were prepared by forming a fibrous aggregate on the side of the effective surface of a structure as mentioned above.

Articles of Comparative Examples were prepared by covering a structure as mentioned above with each of various sheet-like surface materials.

A slip-preventing tape was attached to each non-service surface.

The leak rate, separation state, and hand of each test sample thus prepared were evaluated according to the following methods. The results are shown in Table 3.

Test Methods

A test specimen 8 was set on a movable female waist model 6 as shown in FIG. 7 in such a way as shown in FIG. 8. One hour and two hours after the model was set into motion, 5 g each of artificial blood was injected twice into the specimen through an artificial blood dropping tube 7 to effect injection of a total of 10 g. Leg opening in a forward and backward direction (walking D-D' direction), L and leg opening and closing (C-C' direction) were repeated for a total of 3 hours. Thereafter, leak of the test specimen 8 was checked. The state of separation of the surface material from the absorbent layer was simultaneously checked. The test was made with 5 specimens for each sample.

As to the hand on the side of the effective surface, the sensuous test was made by 5 women to find an average overall rating. The ratings include 5 points for very good hand, 4 points for good hand, 3 points for common hand, 2 points for poor hand, and one point for very poor hand. An average point of five womens' ratings was found.

TABLE 3

| | Sample code | Leak[*1] rate | Separation[*2] distance (mm) | Hand |
| --- | --- | --- | --- | --- |
| Present | B | 1/5 | 0~2 | 4.2 |

TABLE 3-continued

|  | Sample code | Leak[*1] rate | Separation[*2] distance (mm) | Hand |
|---|---|---|---|---|
| Invention | D | 1/5 | 0~1 | 4.6 |
|  | E | 0/5 | 0 | 4.2 |
|  | F | 1/5 | 0~1 | 3.6 |
|  | J | 0/5 | 0~1 | 4.4 |
|  | O | 1/5 | 0~1 | 4.4 |
|  | P | 0/5 | 0 | 4.0 |
|  | S | 0/5 | 0 | 4.4 |
|  | T | 0/5 | 0 | 4.2 |
|  | U | 0/5 | 0~1 | 4.8 |
|  | V | 1/5 | 0~1 | 4.6 |
| Comparative | 1 | 3/5 | 2~14 | 3.8 |
| Example | 3 | 3/5 | 3~11 | 3.8 |
|  | 5 | 3/5 | 3~8 | 4.2 |
|  | 6 | 4/5 | 4~12 | 4.0 |
|  | 8 | 3/5 | 2~5 | 3.2 |
|  | 9 | 4/5 | 3~13 | 2.8 |
|  | 10 | 3/5 | 2~6 | 4.4 |
|  | 12 | 4/5 | 2~15 | 4.4 |
|  | E' | 3/5 | 2~8 | 4.2 |
|  | J' | 4/5 | 4~12 | 4.2 |
|  | O' | 2/5 | 3~6 | 4.4 |
|  | T' | 3/5 | 4~10 | 4.4 |
|  | V' | 3/5 | 2~7 | 4.4 |

(Note)
[*1] shown in terms of number of specimens which leaked/number of specimens tested.
[*2] shown in terms of a range from a minimum value to a maximum value as to five specimens tested.

Measurement method: measured in cross-sections formed by cutting in portions where separation looks visually large and small respectively.

It can be understood from Table 3 that the absorbent articles according to the present invention show excellent leak-proof effects as compared with those of Comparative Examples. These effects were exhibited substantially without the influences of the kind of base material (resin), the type of fibrous aggregate, the avarage fiber diameter, and the basis weight.

This suggests how greatly integration of the surface material and the absorbent layer contributes to the leak-proof effect. Samples showing a separation distance of 2 mm or more include sheets E', J', O', T', and V' formed under the same conditions as in the present invention, and all have respective high leak rates. These certainly suggests usefulness of the present invention in comparison with the conventional absorbent articles covered with a sheet surface material.

Among others, Sample U having a small fiber diameter of 9 μm has gotten a high rating of hand. Those getting high ratings are found overall even as compared with those of Comparative Examples. Thus it was confirmed that they had sufficient hands comparable to those of other surface materials which were developed with emphasis put also on hands as the usual practice.

EXAMPLE 2

Use: Long-Term Service Sanitary Napkin

A laminate of an absorbent layer composed of cotton-like pulp (4 g), four sheets of absorbent paper (2 g), and a water-absorptive polymer (0.5 g), and a leak-proof material consisting of water-proof paper having 8 μm polyethylene laminated was used as the basic structure.

Test specimens were prepared in the same manner as in Example 1.

The test was made in substantially the same manner as in Example 1 except that the artificial blood dropping conditions were set so that 5 g each of the artificial blood was dropped four times at intervals of 1 hour in total of 20 g.

The results are shown in Table 4.

The results suggest that the absorbent articles according to the present invention are excellent in leak-proof effect as in Example 1.

As described in Example 1, it was also confirmed that the absorptivity was not affected by making structural control according to a procedure of using two kinds of resins or varying the fiber diameter in the thickness-wise direction of the fibrous aggregate for the purpose of improving the hand on the side of the effective surface.

TABLE 4

|  | Sample[*1] code | Leak rate | Separation distance (mm) |
|---|---|---|---|
| Present Invention | G | 2/5 | 0~1 |
|  | H | 1/5 | 0~1 |
|  | Q | 1/5 | 0~1 |
|  | R | 2/5 | 0~1 |
|  | W | 0/5 | 0 |
|  | X | 1/5 | 0 |
|  | A/F | 1/5 | 0~1 |
|  | C/F | 1/5 | 0 |
|  | C/I | 2/5 | 0~1 |
|  | A/K | 1/5 | 0~1 |
|  | L/P | 2/5 | 0~1 |
|  | M/P | 2/5 | 0~1 |
| Comparative | 2 | 4/5 | 3~10 |
| Example | 4 | 4/5 | 4~9 |
|  | 7 | 3/5 | 3~11 |
|  | 11 | 3/5 | 3~10 |
|  | 13 | 4/5 | 4~14 |
|  | G' | 4/5 | 3~14 |
|  | H' | 4/5 | 3~12 |
|  | Q' | 4/5 | 5~10 |
|  | R' | 3/5 | 3~16 |
|  | W' | 3/5 | 3~8 |
|  | X' | 3/5 | 3~11 |

(Note)
[*1] A/F indicates that a fibrous aggregate was first integrated on the absorbent layer under the same conditions as in F, and a fibrous aggregate was further integrated thereon under the same conditions as in A (the surface layer on the effective surface side is referred to as A)

EXAMPLE 3

Use: Paper Diaper

Paper diapers were constituted by an absorbent layer composed by cotton-like pulp (30 g), absorbent paper (5 g), a water-absorptive polymer (3 g), a back sheet, and a fixation taper as the basic constituent materials. Test specimens were prepared.

The actual service test was conducted with five specimens for each sample. Leak and shape retention of the surface material and the absorption layer after the use were checked.

The results are shown in Table 5.

As is apparent from the table, effectiveness of integration of the surface material with the absorbent layer according to the present invention was confirmed in the paper diapers of this Example as the absorbent article used under complex movement, just as in the sanitary napkins of Examples 1 and 2.

TABLE 5

|  | Sample code | Leak rate | Separation distance (mm) | Deformation of surface material |
|---|---|---|---|---|
| Present invention | G | 2/5 | 0~3 | slight |
|  | Q | 2/5 | 0~3 | substantially no |
|  | W | 1/5 | 0~2 | substantially no |

TABLE 5-continued

|  | Sample code | Leak rate | Separation distance (mm) | Deformation of surface material |
|---|---|---|---|---|
|  | A/K | 2/5 | 0~2 | substantially no |
|  | N/T | 2/5 | 0~2 | substantially no |
| Comparative Example | 2 | 4/5 | 5~20 | large |
|  | 4 | 4/5 | 5~15 | large |
|  | 7 | 3/5 | 7~10 | large |
|  | 11 | 4/5 | 4~18 | large |

The invention article will be further illustrated below in respect to the embodiment 2.

The measurements of the leak-proof effect and vapor permeability for confirmation of the effects of the present invention were made in accordance with the following methods.

1 Leak-Proof Effect 2 g of pulp, 1.2 g of an absorbent paper, 0.3 g of a liquid-absorptive polymer, and 0.5 g of a surface material were placed on a specimen (leak-proof material) to form a napkin model. 20 g of equine defibrinated blood as the test liquid was dropped on the model, and absorbed therein. A load was appleid onto the model. The load was changed from 5 g/cm² to 150 g/cm² to determine a weight under which leak or ooze from the reverse side of the specimen was first recognized. The determination under a given condition was continued for 3 minutes. When neither leak nor ooze occurred, the load was sequentially increased.

2 Vapor Permeability

Permeability for initial one hour (g/100 cm².hr) was measured in accordance with JIS Z-0208.

EXAMPLE 4 (MELTING METHOD)

Each of various hot-melt resins as shown in Table 6 was molten at higher temperatues than the melting point thereof, and ejected together with hot air of 300° C. onto a preliminarily heated porous base material as shown in Table 6 through a nozzle of 0.3 mm in diameter to effect integretion of them. Thus leak-proof materials were formed. The fiber diameter was controlled by varying the amount of hot air and the ejection pressure. The weight of fibrous aggregate was controlled by varying the ejection time.

The results of determination of leak-proof effect and vapor permeability are shown in Table 6.

TABLE 6

| Porous base material | Hot-melt resin | Bonding method | | Average fiber diameter (μm) | Weight of fibrous aggregate (g/m²) | Leak-proof effect (g/cm²) | Vapor permeability [g/100 cm² · hr] |
|---|---|---|---|---|---|---|---|
| sized paper I wet-machined raw materials | polyethylene | A | | 11 | 10 | 110 | 2.0 |
|  |  |  |  | 12 | 25 | 130 | 1.8 |
|  |  |  |  | 12 | 50 | >150 | 1.2 |
| NBKP pulp sizepine E 0.1%*² aluminum sulfate 2.0% | polypropylene | A | | 11 | 20 | 140 | 1.8 |
|  |  |  |  | 11 | 30 | 150 | 1.6 |
|  |  |  |  | 14 | 30 | 130 | 1.6 |
|  |  |  |  | 18 | 30 | 120 | 1.8 |
|  |  |  |  | 22 | 50 | 120 | 1.9 |
|  | polyester | A | | 11 | 20 | 130 | 2.0 |
|  | polyester | A | | 11 | 20 | 130 | 1.9 |
|  | nylon | A | | 12 | 20 | 130 | 2.1 |
|  | polyethylene-polypropylene rubber | A | | 13 | 20 | 120 | 1.9 |
| sized paper I wet-machined raw materials NBKP pulp RF Size KR45 1.0%*³ aluminum sulfate 2.0% | polyethylene | B | 10% | 12 | 20 | 130 | 1.9 |
|  |  |  | 20 | 12 | 20 | 130 | 1.8 |
|  |  |  | 30 | 12 | 20 | 130 | 1.9 |
|  |  | C | 10% | 14 | 30 | 140 | 1.8 |
|  |  |  | 20 | 14 | 30 | 140 | 1.7 |
|  |  |  | 40 | 14 | 30 | 140 | 1.6 |
|  | polypropylene | B | 20% | 18 | 30 | 130 | 1.8 |
|  |  | C | 20% | 18 | 30 | 130 | 1.7 |
|  |  | B | 20% | 19 | 30 | 130 | 1.5 |
|  |  | C | 20% |  |  |  |  |
| porous film polyethylene film pore diameter: about 0.3 mm porosity: 20% | polyethylene | C | 20% | 16 | 20 | 120 | 1.8 |
|  | polypropylene | C | 20% | 16 | 20 | 120 | 1.9 |
|  | polyester | C | 20% | 16 | 20 | 120 | 1.8 |

(Note)
*¹Bonding method:
A: The fibrous aggregate itself is integrated with the porous base material.
B: The fibrous aggregate is integrated with the porous base material coated with an adhesive (acrylic) at a predetermined proportion. e.g.: "B 20%" means an adhesive-coated area of 20%.
C: The fibrous aggregate integrated with the porous base material is partially subjected to heat embossing to effect melt integration. e.g.: "C 10%" means a heat-embossed area of 10%.
*²rosin sizing agent manufactured by Arakawa Kagaku Kogyo K. K.
*³rosin sizing agent manufactured by Hamano Industry Co., Ltd.

EXAMPLE 5 (SOLVENT METHOD)

Each of various resins as shown in Table 7 was dissolved in THF or DMF in an amount of 9 times the resin weight to prepare a 10 wt. % THF or DMF solution of the resin. The solution was ejected together with compressed air onto porous base materials as shown in Table 7 with a spray gun, and dried to obtain leak-proof materials. The fiber diameter was controlled by varying the amount of air and the ejection pressure. The weight of fibrous aggregate was controlled by varying the ejection time. The results of determination of the leak-proof effect and vapor permeability are shown in Table 7.

actually form a napkin. A portion of each napkin corresponding to the center in the widthwise direction as a base was immersed in equine fibrinated blood to find an uptake distance on the side of the effective surface (on

TABLE 7

| Porous base material | Resin | Solvent | Bonding method | Average fiber diameter (μm) | Weight of fibrous aggregate (g/m²) | Leak-proof effect (g/cm²) | Vapor permeability [g/100 cm² · hr] |
|---|---|---|---|---|---|---|---|
| sized paper I | polyurethane | THF | A | 8 | 5 | 90 | 1.9 |
| | | | | 9 | 10 | 100 | 1.9 |
| | | | | 12 | 15 | 120 | 2.1 |
| | | | | 13 | 20 | 120 | 2.0 |
| | | | | 12 | 30 | 130 | 1.9 |
| | | | | 17 | 30 | 120 | 2.0 |
| | | | | 21 | 30 | 120 | 2.0 |
| | polybutadiene | THF | A | 12 | 10 | 120 | 2.1 |
| | | | | 12 | 20 | 130 | 1.9 |
| | | | | 12 | 50 | >150 | 1.8 |
| | high styrene | DMF | A | 14 | 15 | 120 | 2.1 |
| | vinylidene polyvinyl chloride | DMF | A | 10 | 15 | 120 | 2.0 |
| | | DMF | A | 13 | 15 | 130 | 1.9 |
| sized paper II | polybutadiene | THF | A | 11 | 30 | 120 | 1.8 |
| | | | B  5% | 11 | 30 | 130 | 1.8 |
| | | | B 10 | 17 | 30 | 130 | 1.9 |
| | | | B 20 | 17 | 30 | 120 | 1.8 |
| | | | C 10% | 16 | 30 | 120 | 1.9 |
| | | | C 20 | 17 | 30 | 120 | 1.8 |
| porous film | polyurethane | THF | B  5% | 13 | 20 | 120 | 2.0 |
| | | | C  5% | 14 | 20 | 130 | 2.0 |
| | polybutadiene | THF | A | 13 | 30 | 140 | 2.0 |
| | | | B 20% | 14 | 30 | 140 | 1.9 |
| | | | C 20% | 13 | 30 | 130 | 1.9 |

COMPARATIVE EXAMPLE 1

The same procedures as in Example 6 were made as to porous base materials not integrated with any fibrous aggregate, and non-porous base materials. Results are shown in Table 8.

the side of the fibrous aggregate) after 10 minutes.
A smaller uptake distance indicates a better result.
(2) Leak-proof Properties
① Test napkins as shown in FIGS. 17 to 19 to 25 were tentatively prepared using, as essential materials, base materials of the specimens having respective fi-

TABLE 8

| Base material | Remarks | Basis weight (g/m²) | Leak-proof effect (g/cm²) | Vapor permeability [g/100 cm² · hr] |
|---|---|---|---|---|
| sized paper I | wet-machined raw materials NBKP pulp sizepine E 1.0%* aluminum sulfate 2.0% | 30 | 40 | 2.2 |
| sized paper II | wet-machined raw materials NBKP pulp RF size KR-45 1.0%** aluminum sulfate 2.0% | 30 | 50 | 2.1 |
| porous film | polyethylene film pore diameter: about 0.3 mm porosity: 2.0% | 25 | 10 | 2.1 |
| polymer-laminated waterproof paper | sized paper I/8 μm polyethylene laminate | 37 | >150 | 0 |
| | sized paper II/10 μm polyethylene laminate | 39 | >150 | 0 |
| polyethylene film | 8 μm non-laminated film | 25 | >150 | 0 |

*rosin sizing agent manufactured by Arakawa Kagaku Kogyo K. K.
**rosin sizing agent manufactured by Hamano Industry Co., Ltd.

The invention article will be below illustrated in respect to the embodiment 3.

Measurements of liquid diffusion capacity and leak-proof properties for confirmation of the effects of the present invention were made in accordance with the following methods.

(1) Diffusion Capacity (application of the Klemm Test Method)

Specimens having respective fibrous aggregates integrated under various conditions were each cut to a width of 15 cm in such a width-wise direction as to brous aggregates integrated under various conditions, 2 g of surface material pulp, 1.2 g of absorbent paper, and 0.3 g of a liquid-absorptive polymer. Subsequently, each test napkin was set in a V form (90°) close to the actually worn form as shown in FIG. 18. 10 cc of equine defibrinated blood was injected from the top portion of the test napkin under a pressure of 50 g/cm² corresponding to the actual wearing pressure separately twice with each 5 cc/30 min. It was allowed to stand as it was. After one hour, the state of side leak, which is leak from the sides of the absorbent article, was observed.

No side leak is, of course, a good result.

The test was made with 10 specimens for each test sample. The results are shown in terms of the number of specimens which showed side leak of the ten specimens. For example, 2/10 indicates that two specimens of the ten specimens showed occurrence of leak.

2 Evaluation with Dynamic Human Body Model

A test specimen 10 as prepared in Leak-Proof Properties 1 was set on a movable female waist model 6 as shown in FIG. 7 in such a way as shown in FIG. 8. One hour and two hours after the model was set into motion, 5 g each of an artificial blood was injected twice into the specimen through an artificial blood dropping tube 9 to effect injection of a total of 10 g. Leg opening in a forward and backward direction (walking D—D' direction), and leg opening and closing (C—C' direction) were repeated for a total of 3 hours. Therefore, leak of the test specimen 10 was checked. The test was made with 10 specimens for each test sample. The results are shown in terms of the number of specimens which showed side leak of the ten specimens.

EXAMPLE 6 (MELTING METHOD)

Each of various hot-melt resins as shown in Table 9 was molten at a higher temperature than the melting point thereof, and ejected together with hot air of 300° C. onto a preliminarily heated nonwoven fabric through a nozzle of 0.3 mm in diameter to effect integration of them. Thus surface materials were formed. The fiber diameter was controlled by varying the amount of hot air and the ejection pressure. The weight of fibrous aggregate was controlled by varying the ejection time. The same non-woven fabric as that of No. 6 in Comparative Example 2 which will be given later was used in those of FIGS. 17 and 19 to 21, while the same non-woven fabric as that of No. 2 was used in those of Figs. 22 to 25.

Evaluation results are shown in Table 9.

TABLE 9

| Hot-melt resin | Structure of napkin | Basis weight of fibrous aggregate | | Fiber diameter of fibrous aggregate (μm) | Thickness of both end portions (mm) |
|---|---|---|---|---|---|
| | | Both end portions (g/m²) | Middle portions (g/m²) | | |
| polyethylene | FIG. 17 | 5 | — | 7 | 0.3 |
| | FIG. 17 | 20 | — | 9 | 0.5 |
| | FIG. 17 | 50 | — | 13 | 0.7 |
| | FIG. 17 | 50 | — | 28 | 0.5 |
| | FIG. 19 | 20 | — | 9 | 0.6 |
| | FIG. 22 | 20 | — | 9 | 0.6 |
| | FIG. 23 | 20 | — | 9 | 0.5 |
| polypropylene | FIG. 20 | 30 | 3 | 7 | 0.5 |
| | FIG. 21 | 40 | 3 | 18 | 0.9 |
| | FIG. 17 | 10 | — | 11 | 0.7 |
| | FIG. 24 | 20 | 5 | 14 | 0.8 |
| polyester | FIG. 17 | 30 | — | 10 | 0.3 |
| nylon | FIG. 25 | 50 | 5 | 14 | 0.8 |
| polybutadiene | FIG. 22 | 20 | — | 11 | 0.4 |
| ethylene-vinyl acetate | FIG. 23 | 20 | — | 18 | 0.5 |

| Hot-melt resin | Bonding*¹ method | Additive | Diffusion capacity (mm) | Leak-proof properties | |
|---|---|---|---|---|---|
| | | | | 1 | 2 |
| polyethylene | A 10% | — | 0 | 0/10 | 2/10 |
| | B 10% | titanium white 0.3% | 0 | 0/10 | 0/10 |
| | C | — | 0 | 0/10 | 0/10 |
| | C | calcium carbonate 5% | 0 | 0/10 | 0/10 |
| | B 10% | — | 0 | 0/10 | 0/10 |
| | B 10% | — | 0 | 0/10 | 0/10 |
| | B 10% | — | 0 | 0/10 | 0/10 |
| polypropylene | C | — | 0 | 0/10 | 0/10 |
| | C | calcium carbonate 1% | 0 | 0/10 | 0/10 |
| | A 20% | — | 0 | 0/10 | 1/10 |
| | B 10% | — | 0 | 0/10 | 0/10 |
| polyester | A 10% | — | ~1 | 0/10 | 0/10 |
| nylon | A 10% | — | ~1 | 0/10 | 0/10 |
| polybutadiene | B 40% | — | 0 | 0/10 | 0/10 |
| ethylene-vinyl acetate | B 30% | titanium yellow 1% | ~1 | 0/10 | 0/10 |

(Note)
*¹"A" indicates what % the use of an adhesive accounts for. For example, "A 10%" means that integration was effected with a 10% area where an adhesive was used in combination. In a similar way, "B 10%" means that melt bonding by heat-embossing was combinedly used in a 10% area. "C" means that only welding with a fibrous aggregate itself was effected.

EXAMPLE 7 (SOLVENT METHOD)

Each of various resins as shown in Table 10 was dissolved in THF or DMF in an amount of 9 times the resin weight to prepare a 10 wt. % THF or DMF solution of the resin. The solution was ejected together with compressed air onto non-woven fabrics with a spray gun, and dried to obtain surface materials. The fiber diameter was controlled by varying the amount of air and the ejection pressure. The weight of fibrous aggregate was controlled by varying the ejection time. The same non-woven fabrics as in Example 9 were used.

Evaluation results are shown in Table 10.

properties. Thus side leak was observed in 5 to 7 specimens of 10 specimens.

As to Nos. 6 and 7, the diffusing capacities were low

TABLE 10

| Resin | Solvent | Structure of napkin | Basis weight of fibrous aggregate | | Fiber diameter of fibrous aggregate (μm) | Thickness of both end portions (mm) |
|---|---|---|---|---|---|---|
| | | | Both end portions (g/m²) | Middle portions (g/m²) | | |
| polyurethane | THF | FIG. 17 | 5 | — | 7 | 0.1 |
| | | FIG. 19 | 10 | — | 9 | 0.2 |
| | | FIG. 22 | 20 | — | 10 | 0.2 |
| | | FIG. 23 | 50 | — | 15 | 0.4 |
| | | FIG. 20 | 30 | 3 | 13 | 0.3 |
| polybutadiene | THF | FIG. 17 | 30 | — | 9 | 0.4 |
| | | FIG. 19 | 20 | — | 8 | 0.2 |
| | | FIG. 21 | 30 | 5 | 11 | 0.3 |
| | | FIG. 24 | 30 | 5 | 11 | 0.2 |
| | hexane | FIG. 25 | 30 | 5 | 8 | 0.3 |
| high styrene | THF | FIG. 17 | 20 | — | 13 | 0.6 |
| ethylene-propylene rubber | toluene | FIG. 17 | 20 | — | 13 | 0.5 |

| Resin | Bonding method | Additive | Diffusion capacity (mm) | Leak-proof properties | |
|---|---|---|---|---|---|
| | | | | 1 | 2 |
| polyurethane | C | fluorine-containing surface active agent 0.3% | 0 | 0/10 | 1/10 |
| | C | — | ~1 | 0/10 | 1/10 |
| | C | fluorine-containing surface active agent 0.3% | 0 | 0/10 | 0/10 |
| | C | — | ~1 | 0/10 | 0/10 |
| | C | — | ~1 | 0/10 | 0/10 |
| polybutadiene | C | pigment (blue) 0.1% | 0 | 0/10 | 0/10 |
| | A 10% | Aerosil 2% | 0 | 0/10 | 0/10 |
| | A 10% | — | 0 | 0/10 | 0/10 |
| | C | — | 0 | 0/10 | 0/10 |
| | C | — | 0 | 0/10 | 0/10 |
| high styrene | C | — | ~1 | 0/10 | 0/10 |
| ethylene-propylene rubber | C | — | ~1 | 0/10 | 0/10 |

COMPARATIVE EXAMPLE 2

Various non-woven fabrics having no fibrous aggregate integrated therewith were evaluated in the same manner as in Example 9. Results are shown in Table 11.

(because of the use of a hydrophobic fiber) to provide good results, and better test results of leak-proof properties 1 were obtained due to the effects of their diffusion capacities. However, in the test of leak-proof properties 2 side leak was found in 5 to 6 specimens because blood from the inside of the absorbent article was

TABLE 11

| No. | Fiber constituting surface material substrate | | | | Total basis weight (g/m²) | Diffusion capacity (mm) | Leak-proof properties | |
|---|---|---|---|---|---|---|---|---|
| | First fiber | Fiber diameter (μm) | Second fiber | Fiber diameter (μm) | | | 1 | 2 |
| 1 | rayon | 14 | — | | 23 | 15 | 5/10 | 6/10 |
| 2 | rayon | 16 | — | | 27.5 | 17 | 5/10 | 7/10 |
| 3 | rayon | 14 | ES | 16 | 20 | 13 | 4/10 | 6/10 |
| 4 | rayon | 14 | polypropylene | 18 | 18 | 12 | 4/10 | 5/10 |
| 5 | rayon | 20 | polyethylene | 12 | 22 | 15 | 4/10 | 5/10 |
| 6 | polypropylene | 18 | ES | 16 | 18 | ~1 | 2/10 | 5/10 |
| 7 | polypropylene | 16 | polyester | 11 | 20 | ~1 | 3/10 | 6/10 |
| 8 | polyethylene | 11 | — | | 25 | 0 | 10/10 | 10/10 |

No. 1, 4, 5: acrylic binder type non-woven fabric
No. 2: wet-spun-bonded 100% rayon non-woven fabric
No. 3, 6, 7: no-binder hot-melt type non-woven fabric
No. 8: spun-bonded non-woven fabric
ES: polyethylene-polypropylene conjugated fiber
No. 7 polyester: low melting point polyester
Nos. 1, 3, 5, 6, and 8 herein mentioned have a structure (without any fibrous aggregate) as shown in FIGS. 17 and 19 to 21.
Nos. 2, 4, and 7 have a structure (without any fibrous aggregate) as shown in FIGS. 22 to 25.

The rayon surface materials, of the conventional surface materials, as shown in Table 11, are hydrophilic in themselves and hence they have high diffusion capacities (ooze in a non-woven fabric) and poor leak-proof pushed out through the surface material.

As to No. 8, the diffusion capacity was favorable due to the completely hydrophobic nature, but blood was not introduced into the absorbent article through the surface material with flow of the whole blood along the surface.

In summary, the conventional surface materials are designed to simultaneously have 1 sufficient interfiber spaces and 2 sufficient wettability for the propose of rapid absorption of menstrual blood.

Therefore, diffusion through spaces between fibers of the non-woven fabric cannot be avoided. As soon as blood is just to be pushed out of the absorbent article by a change of the groin form (specifically, the severest state is one in the case of ride on a bicycle), pushing out of blood onto the surface is ready since the surface itself has spaces through which blood permeated fast. Repetition of this cause side leak from the side of the V form of the worn napkin as shown in FIG. 27(b).

Even if both the end portions are subjected to an easily imaginable water-repelling treatment, the effect of it is very small because of large spaces.

As against these in Comparative Example, the absorbent articles of the present invention were observed to have excellent leak-proof properties as shown in Tables 9 and 10.

These effects are not gravely affected by the resin, the structure, the weight of fibrous aggregate, the fiber diameter, the thickness, the bonding method, and the additives.

In other words, effective side leak prevention can be basically attained by formation, in both end portions of the surface material, of leak-proof walls (structures) having heretofore impossible minute spaces enough to prevent blood from being pushed out from the absorbent article by integrating an aggregate of a hydrophobic fiber of 1 to 40 μm in diameter at 5 g/m² on the effective face side and at least in the both end portions on the lateral sides (on the long sides) of the uppermost layer.

In short, according to the present invention, side leak prevention can be materialized while maintaining a feature of a surface with a high absorption rate not allowing blood to flow thereon, which has been in a stage of development.

Use of an adhesive or welding in the bonding method, various surface-active agents as the additives, and a pigment does not present any problems.

The invention will be illustrated below in respect to the embodiment 4.

EXAMPLE 8 (MELTING METHOD)

Each sample, shown in Table 12, was prepared in the same manner as shown in Example 4, except that a thermoplastic resin in Table 12 was integrated with the lowermost sheet on the side not to contact the skin of a user. Test results are shown in Table 12. note:
1: A reference to A means a structure shown in FIG. 28a and B means that of FIG. 29.
2: Bonding method:
   a: The fibrous aggregate itself is integrated with the lowermost sheet.
   b: The fibrous aggregate is integrated with the lowermost sheet coated with an adhesive (acrylic) at a predetermined proportion.
      e.g.: "b 30%" means an adhesive-coated area of 30%.
   c: The fibrous aggregate is integrated with the lowermost sheet and then is partially subjected to the heat embossing to effect the melt integration.
      e.g.: "c 20%" means a heat-embossed area of 20%.
3: A value means an extent of samples in which a leak appeared among 10 test samples. A value of 2/10 indicates that 2 samples encountered the leaking among 10 test samples.

EXAMPLE 9 (SOLVENT METHOD)

Each sample, shown in Table 13, was prepared in the same way as mentioned in Example 5 so that a resin shown in Table 13 might be integrated only with the lowermost sheet on the side not to contact with the skin of a user. Test results are shown in Table 13.

TABLE 12

| Sample No. | structure of sample *1 | resin for the lowermost sheet | fiber aggregate resin | average diameter (μ) | weight | integration method *2 method | extent | prevention of slipping-out when dried | prevention of slipping-out when absorbed | leaking extent *3 |
|---|---|---|---|---|---|---|---|---|---|---|
| 1 | A | polyethylene- | polyurethane | 3μ | 20 g/m² | c | 20% | 3 mm | 3 mm | 2/10 |
| 2 | | polypropylene | | 21μ | 22 g/m² | | 20% | 2 mm | ~0 mm | 0/10 |
| 3 | | complex fiber | | 42μ | 19 g/m² | | 20% | 3 mm | 2 mm | 1/10 |
| 4 | | (ES fiber) | | 48μ | 20 g/m² | | 20% | 6 mm | 4 mm | 1/10 |
| 5 | | | | 15μ | 31 g/m² | a | — | ~0 mm | ~0 mm | 0/10 |
| 6 | | | | 20μ | 53 g/m² | | | ~0 mm | ~0 mm | 0/10 |
| 7 | | | | 2μ | 6 g/m² | | | 5 mm | 3 mm | 1/10 |
| 8 | | | | 10μ | 15 g/m² | | | 3 mm | 4 mm | 2/10 |
| 9 | | | | 21μ | 19 g/m² | b | 30% | 4 mm | 3 mm | 2/10 |
| 10 | | | | 33μ | 15 g/m² | | 40% | 5 mm | 4 mm | 2/10 |
| 11 | | polyester fiber | | 16μ | 29 g/m² | a | — | ~0 mm | ~0 mm | 0/10 |
| 12 | B | wet method paper of pulp and polyester | | 17μ | 18 g/m² | a | — | 2 mm | ~0 mm | 0/10 |
| 13 | | polyethylene film | | 15μ | 22 g/m² | c | 20% | ~0 mm | ~0 mm | 0/10 |
| 14 | A | ES fiber | polybutadiene | 15μ | 32 g/m² | a | — | ~0 mm | ~0 mm | 0/10 |
| 15 | | polyester fiber | | 18μ | 31 g/m² | a | — | ~0 mm | ~0 mm | 0/10 |
| 16 | B | polyethylene film | | 15μ | 28 g/m² | a | — | ~0 mm | ~0 mm | 0/10 |
| 17 | A | polyester fiber | ethylene-propylene rubber | 16μ | 33 g/m² | a | — | 2 mm | 2 mm | 0/10 |

TABLE 13

| Sample No. | structure of sample *1 | resin for the lowermost sheet | fiber aggregate | | | | integration method *2 | | prevention of slipping-out | | leaking extent *3 |
|---|---|---|---|---|---|---|---|---|---|---|---|
| | | | resin | solvent | average diameter (μ) | weight | method | extent | when dried | when absorbed | |
| 18 | A | ES fiber | poly-urethane | THF | 1μ | 5 g/m² | c | 20% | 5 mm | 6 mm | 3/10 |
| 19 | | | | | 16μ | 26 g/m² | | 16% | 2 mm | 3 mm | 1/10 |
| 20 | | | | | 31μ | 13 g/m² | | 23% | 2 mm | 2 mm | 1/10 |
| 21 | | | | | 18μ | 27 g/m² | a | — | ~0 mm | ~0 mm | 0/10 |
| 22 | | | | | 31μ | 15 g/m² | | | ~0 mm | ~0 mm | 0/10 |
| 23 | | polyester fiber | | | 21μ | 31 g/m² | b | 20% | 1 mm | 2 mm | 1/10 |
| 24 | B | wet method paper of pulp and polyester | | | 22μ | 30 g/m² | | | 2 mm | 3 mm | 1/10 |
| 25 | | polyethylene film | | | 19μ | 28 g/m² | | | 2 mm | 2 mm | 0/10 |
| 26 | A | polyester fiber | poly-butadiene | THF | 18μ | 25 g/m² | a | — | ~0 mm | ~0 mm | 1/10 |
| 27 | | | | | 30μ | 14 g/m² | | | ~0 mm | ~0 mm | 1/10 |
| 28 | | | | | 21μ | 30 g/m² | c | 20% | ~0 mm | ~0 mm | 1/10 |
| 29 | | | | | 22μ | 43 g/m² | | 40% | 1 mm | 2 mm | 1/10 |
| 30 | B | wet method paper of pulp and rayon | | | 31μ | 16 g/m² | a | — | ~0 mm | ~0 mm | 0/10 |
| 31 | | polyethylene film | | | 29μ | 19 g/m² | | | ~0 mm | ~0 mm | 0/10 |
| 32 | A | ES fiber | high impact polystyrene | DMF | 15μ | 21 g/m² | a | 20% | 4 mm | 5 mm | 2/10 |
| 33 | | polyester fiber | | | 13μ | 22 g/m² | | | 3 mm | 4 mm | 2/10 |

The embodiments of the invention in which an exclusive property or privilege is claimed are defined as follows:

1. A sanitary article which comprises:
   an absorbent layer,
   a leakproof sheet substantially surrounding said absorbent layer, and
   a surface sheet encasing said absorbent layer and said leakproof sheet,
   whereby said sanitary article consists of hydrophobic, thermoplastic porous fibers fixed on respective surfaces of at least one of said absorbent layer, leakproof sheet and surface sheet, such that said fibers are in direct contact with said respective surfaces.

2. The sanitary article of claim 1, wherein said fibers have a thickness of from 1 to 40 μm and a weight of from 3 to 50 g/m².

3. A method of preparation of an absorbent sanitary article which comprises:
   providing an absorbent material to be used as an absorbent in an absorbent sanitary article, a leakproof sheet of material to be used to substantially surround said absorbent material and a surface sheet of material to ultimately encase said absorbent and leakproof materials,
   fixing to respective surfaces of at least one of said absorbent material, leakproof sheet of material and surface sheet of material by fiber welding a hydrophobic, thermoplastic porous fiber such that said fiber is in direct contact with said respective surfaces,
   and fabricating said absorbent sanitary article by substantially surrounding said absorbent material with said leakproof sheet and thereafter encasing said resulting composite with said surface sheet.

4. The method according to claim 3, wherein said thermoplastic fibers are fiber welded to said respective surfaces by melting a thermoplastic resin to form a molten resin, ejecting said molten resin with air at a temperature of from 200° to 400° C., through a nozzle having a plurality of fine openings of 100 μm to 500 μm, onto said respective surface.

5. The method according to claim 3, wherein said thermoplastic fibers are fiber welded to said respective surfaces by dissolving a thermoplastic resin in a suitable solvent to form a solution, spraying said solution onto said respective layers to become fixed thereto and drying.

* * * * *